United States Patent [19]
Friend

[11] 3,982,546
[45] Sept. 28, 1976

[54] DEVICE FOR DRAINING A BODY CAVITY

[76] Inventor: John H. Friend, 10200 Arno Road, Galt, Calif. 95632

[22] Filed: Feb. 28, 1975

[21] Appl. No.: 554,173

[52] U.S. Cl. .......................... 128/350 R; 128/240; 128/275
[51] Int. Cl.² ........................................ A61M 27/00
[58] Field of Search ..................... 128/276–278, 128/240, 247, 348–351, 2 F, 295, 275

[56] References Cited
UNITED STATES PATENTS

| | | | |
|---|---|---|---|
| 2,822,808 | 2/1958 | Boone | 128/276 |
| 3,051,176 | 8/1962 | Alberti | 128/276 |
| 3,115,138 | 12/1963 | McElvenny et al. | 128/278 |
| 3,467,095 | 9/1969 | Ross | 128/214.2 |
| 3,626,928 | 12/1971 | Hohokus et al. | 128/278 X |
| 3,722,503 | 3/1973 | Hovick | 128/295 X |
| 3,752,158 | 8/1973 | Kariher | 128/278 |
| 3,800,799 | 4/1974 | McWhorter | 128/349 R |

FOREIGN PATENTS OR APPLICATIONS

| | | | |
|---|---|---|---|
| 330,284 | 12/1920 | Germany | 128/349 R |

*Primary Examiner*—Dalton L. Truluck
*Attorney, Agent, or Firm*—John H. Crowe

[57] ABSTRACT

An intake tube is inserted into a cavity in a patient's body to withdraw fluid therefrom, and means including an outlet tube cooperates with the intake tube to form a passage that is connected to a vacuum source to withdraw the body fluid. The outlet tube has an outlet port for releasable connection to the vacuum source, and a removable plug closes the outlet port when a vacuum is not needed. A thin-walled, flexible reservoir communicates with said passage to accumulate fluid that may flow from the body cavity in the absence of a vacuum. In some embodiments of the invention, the reservoir encloses the two confronting ends of the intake tube and the outlet tube, the arrangement being such that when a vacuum is applied to the outlet tube, fluid flows directly from the intake tube to and through the outlet tube; and in the absence of a vacuum, fluid flows from the intake tube directly to the reservoir. In some embodiments an input tube introduces irrigating fluid into the body cavity, the irrigating fluid being withdrawn by the intake tube.

16 Claims, 15 Drawing Figures

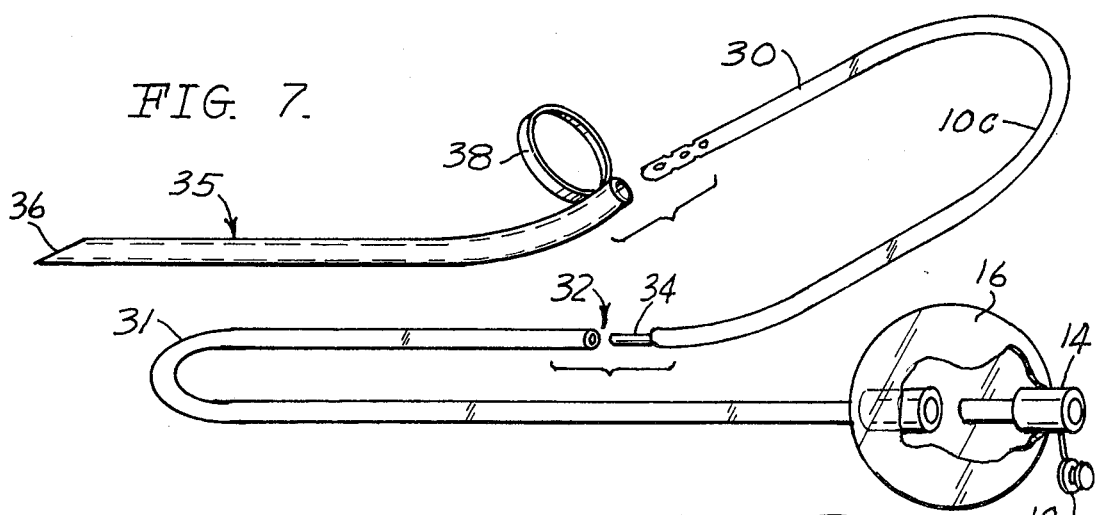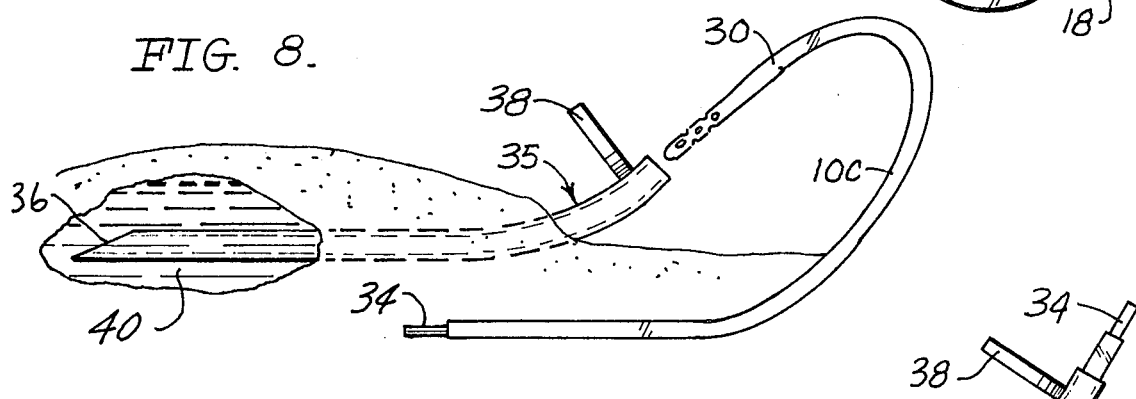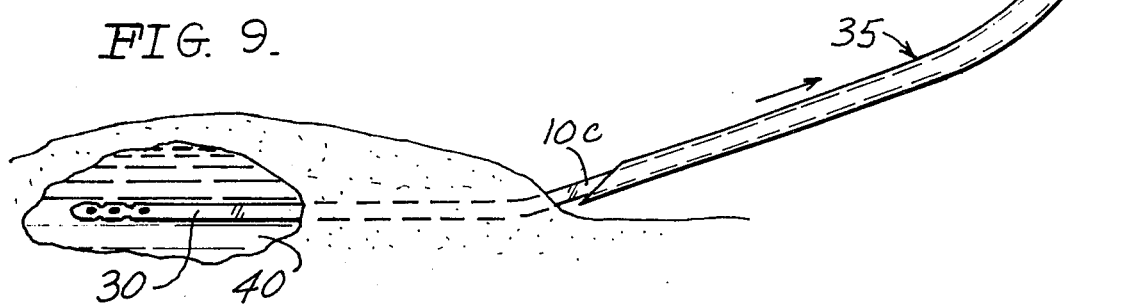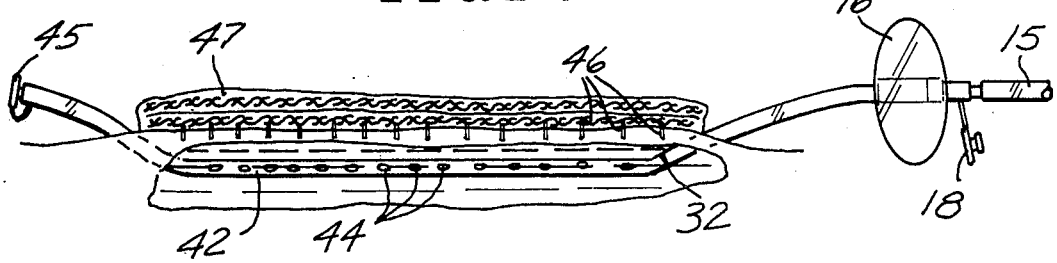

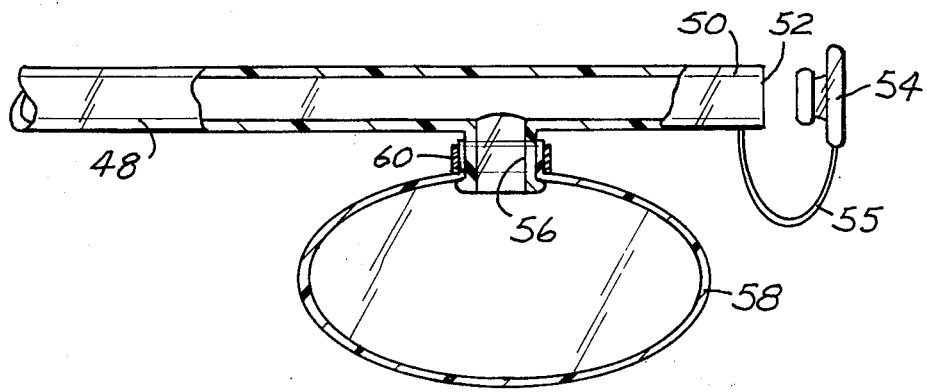
FIG. 11.
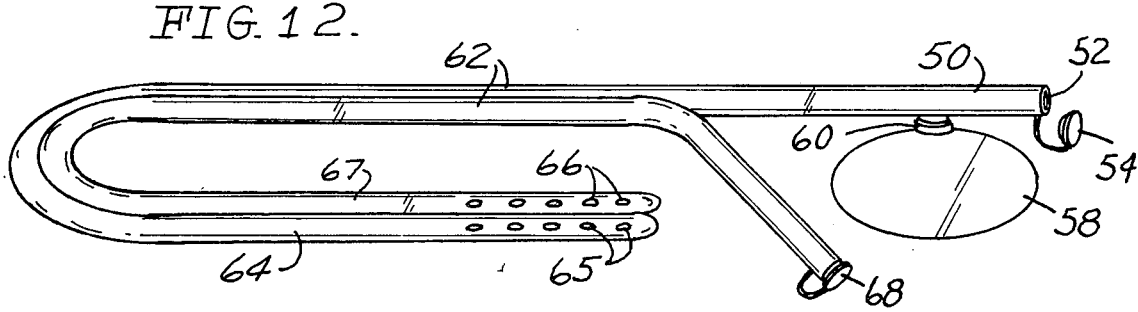
FIG. 12.
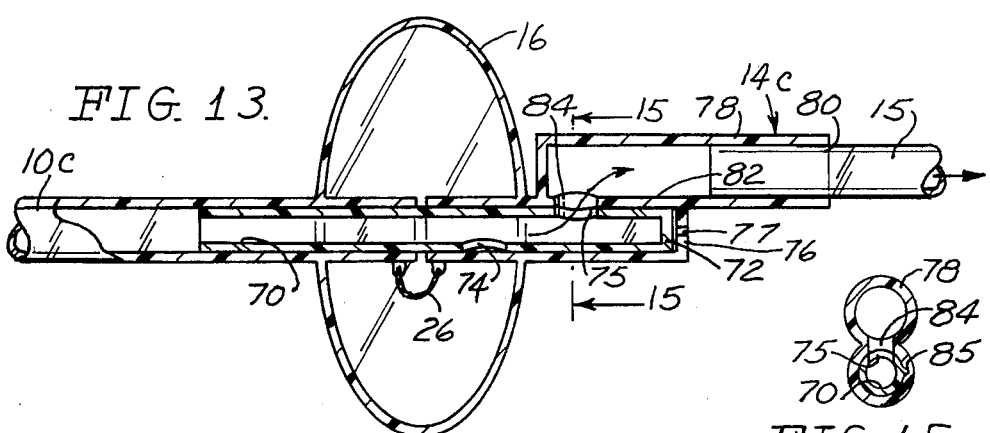
FIG. 13.
FIG. 15.
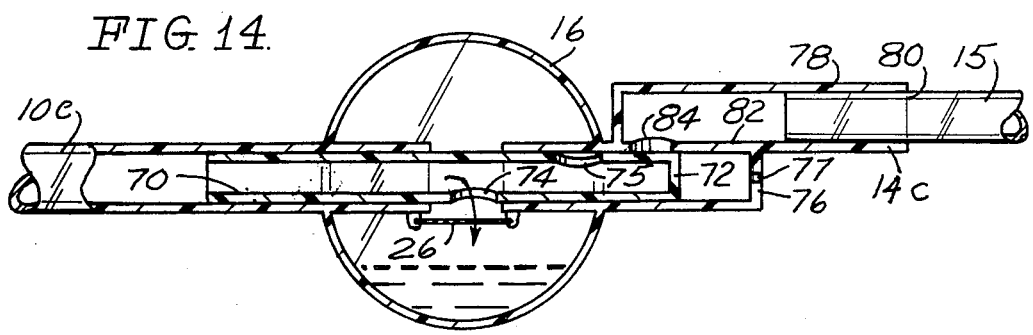
FIG. 14.

DEVICE FOR DRAINING A BODY CAVITY

BACKGROUND OF THE INVENTION

This invention relates to a tubular device for draining fluid from a cavity in the body of a patient, which cavity, for example, may be the stomach, the bladder, an abscess, or a sutured wound.

It is common practice in the medical art to insert an intake tube into a body cavity of a patient and to place the intake tube in communication with a vacuum source to drain fluid from the cavity. The vacuum source may be a manually operated syringe, but more commonly a wall outlet of a vacuum system is conveniently available.

If the body cavity is the stomach and the intake tube is inserted through the patient's nose, no problem arises if the drainage period is brief. In some instances, however, drainage from the stomach is required for a relatively long period of time, for example, during a prolonged surgical operation; and a problem arises because prolonged application of vacuum to the intake tube has a serious eroding effect on the stomach wall.

If the body cavity is the bladder, the intake tube is a catheter, which may be equipped with an inflatable cuff. The catheter normally drains into a drainage receptacle, but it is commonly desirable to take the catheter away from the drainage receptacle periodically to permit the patient to be mobile. At such times the bladder continues spontaneous flow of urine, and the problem arises of how to prevent indiscriminate release of the urine into the environment. One common expedient is to release the urine into a paper cup, and another expedient that is employed at times is to tie a rubber glove to the catheter to serve as a receiver.

If the body cavity is an abscess, the problem is to insert a rubber-like intake tube through the flesh of the patient into the region of the abscess. Commonly, a scalpel is used to make an incision for this purpose, but the insertion of the intake tube through the incision is usually awkward and time consuming.

In some situations it is desirable not only to drain a body cavity, but also to introduce fluid into the cavity periodically for treatment or for irrigation of the cavity. One example is when the body cavity is the healing zone beneath sutures that close a wound.

SUMMARY OF THE INVENTION

A primary object of the invention is to dispose of the drainage of fluid from a body cavity without releasing the drainage to the environment during the periods of time when it is necessary to interrupt the normal disposal of the drainage. This object is accomplished by incorporating a reservoir into the structure of the drainage device for temporary accumulation of the drained fluid. Thus, when the normal disposal of the drainage fluid is interrupted, the outlet port of the device is closed to prevent escape of fluid to the environment, and the drained fluid then accumulates in the reservoir. In all forms of the invention, the drainage device comprises an intake tube for insertion into a body cavity, an outlet tube for releasable connection to a drainage receptacle or to a vacuum source, a reservoir to receive the drained fluid when the releasable connection is interrupted, and, finally, means to cut off the outlet port of the outlet tube when the releasable connection is not employed.

In one embodiment of the invention, the intake tube and the outlet tube are continuous to form a fixed channel to the outlet port of the outlet tube, and the reservoir communicates with this channel laterally thereof. The channel has a somewhat enlarged portion that is formed with a downwardly directed drainage nipple, and a flexible reservoir is releasably attached to the nipple. When it is necessary to interrupt the use of a drainage receptacle or to disconnect the vacuum source from the outlet port of the outlet tube, the drainage accumulates in the reservoir and the outlet port is closed in some suitable manner to prevent escape of the fluid into the environment. When normal disposal of the drainage is resumed, first the reservoir empties and then flow of the drainage fluid resumes through the outlet tube.

In other forms of the invention, confronting ends of the intake tube and the outlet tube, respectively, are enclosed by a flexible, thin-walled reservoir. Normally the confronting tube ends are telescoped together to form a drainage passage that bypasses the flexible reservoir. When normal disposal of the drainage is to be interrupted, however, the outlet port of the outlet tube is cut off and the two confronting tube ends are separated to permit the intake tube to drain directly into the reservoir. Such drainage into the reservoir occurs spontaneously when, as is often the case, the pressure in the body cavity exceeds atmospheric pressure. When such a device is employed to drain the stomach during prolonged surgery, a vacuum is applied initially for only a brief period to empty the stomach and thereafter the vacuum is cut off to avoid eroding the stomach wall, the ensuing spontaneous drainage being accumulated in the reservoir of the device.

In some practices of the invention, a valve is provided in the flexible reservoir between the confronting ends of the intake tube and the outlet tube, respectively. In one such embodiment of the invention, the valve is a three-way valve that has one position to direct the drainage flow from the intake tube to the outlet tube, thus bypassing the reservoir. At its other position, the valve causes the intake tube to discharge into the reservoir. In another embodiment, the valve is adjustable to one position to discharge the intake tube into the reservoir and simultaneously to cut off the outlet port. At its alternate position the valve opens the outlet port and places the intake tube in direct connection therewith.

Some practices of the invention not only provide for draining a body cavity, but also provide for introducing fluid into the cavity. In one such embodiment of the invention, only an intermediate portion of the intake tube is apertured to drain a wound in the healing region below the sutures that close the wound. The far end of the intake tube lies outside the body of the patient and is normally closed for the drainage operation. To irrigate the wound, the far end of the intake tube is opened to receive irrigation fluid. A releasable joint in the intake tube permits the far end of the intake tube to be withdrawn separately from the near end of the tube.

Another embodiment of the invention employs a dual passage tube for insertion into a body cavity. One passage of the dual tube functions as an intake tube in the usual manner. The other passage of the dual tube is normally closed at its outer end, but may be opened for the purpose of introducing fluid into the body cavity.

The features and advantages of the invention may be understood from the following detailed description and the accompanying drawings.

BRIEF DESCRIPTION OF THE DRAWINGS

In the drawings, which are to be regarded as merely illustrative:

FIG. 7 is a perspective view, partly in section, of an embodiment of the invention that may be used to drain an abscess, the intake tube being illustrated as being made in two sections that are interconnected by a quick-disconnect joint;

FIG. 8 shows how a tubular needle may be thrust into an abscess to facilitate the insertion of the leading section of the intake tube;

FIG. 9 illustrates how the tubular needle may be withdrawn from the abscess after the intake tube is installed in the abscess;

FIG. 10 is a view, largely in section, showing how an intermediate portion of the intake tube may be apertured for draining the healing zone beneath the sutures of a wound with the far end of the intake tube extending to the exterior of the patient's body to be available to receive the fluid to treat or irrigate the wound;

FIG. 11 is a fragmentary sectional view showing how a flexible reservoir may be mounted on a downwardly directed nipple of the outlet tube of a drainage device;

FIG. 12 is a perspective view illustrating an embodiment of the invention that employs a dual tube, one passage of the dual tube being employed to withdraw fluid from a body cavity and the other passage being available for introducing a fluid into the body cavity;

FIG. 13 is a fragmentary sectional view of a valve incorporated in a drainage device, the valve being adjusted to place the intake tube in communication with the suction source instead of the flexible reservoir;

FIG. 14 is a similar view of the same valve at an alternate adjustment for cutting off the outlet port of the outlet tube and at the same time diverting the flow from the intake tube into the flexible reservoir; and FIG. 15 is a transverse section taken along the line 15—15 of FIG. 13.

BRIEF DESCRIPTION OF THE SELECTED EMBODIMENTS OF THE INVENTION

Figure 1:
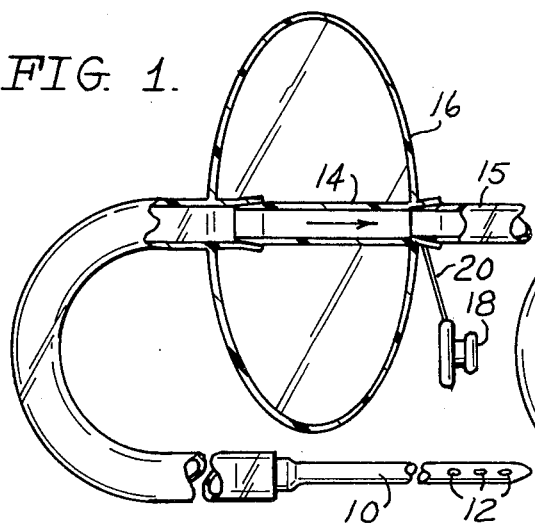
FIG. 1 is a view partly in side elevation and partly in section illustrating an embodiment of the invention in which a flexible thin-walled reservoir is interposed between confronting ends of the intake tube and the outlet tube, respectively, the confronting tube ends being shown as telescoped together for suction drainage of a body cavity.
Figure 2:
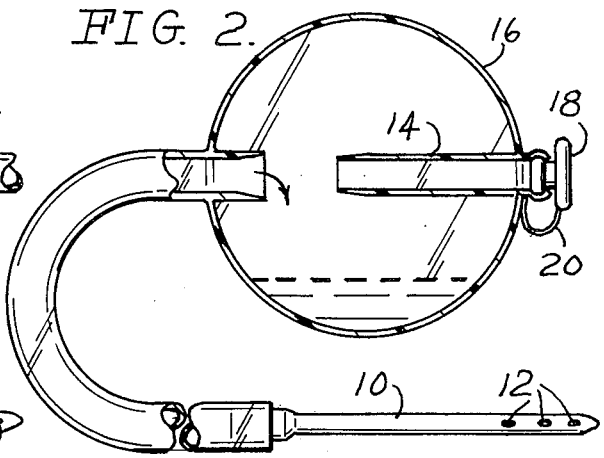
FIG. 2 is a similar view showing the confronting ends of the intake tube and the outlet tube separated to permit the intake tube to discharge into the flexible reservoir.

FIGS. 1 and 2 illustrate an embodiment of the invention which may, for example, be used advantageously as a nasogastric device to withdraw material from the stomach of a patient. The device includes what may be termed an intake tube 10 of soft pliable rubber-like material having intake ports or apertures 12 near its inner end. The intake tube 10 may, for example, be of a length within the range of 26–36 inches for insertion through a patient's nose into the patient's stomach. The device further includes what may be termed an outlet tube 14 that has an outlet port for connection to a suitable vacuum source. For example, a suitable syringe or hand pump may be connected to the outlet port. In the construction shown, the outlet tube 14 releasably telescopes over the end of a suction tube 15 that is plugged into a wall fitting (not shown) of a conventional hospital vacuum system.

The inner ends of the intake tube 10 and the outlet tube 14, respectively, are enclosed by a thin-walled flexible reservoir 16, the opposite walls of which embrace the two tubes and are suitably bonded thereto in a liquid-tight manner. The reservoir may be made of thin latex and in this instance is transparent or nearly transparent for visual observation of the two tube ends.

When the device is used for suction drainage of a patient's stomach, the outlet tube 14 cooperates with the intake tube 10 to form a continuous channel to the vacuum source, and any suitable provision for releasably connecting the outlet tube to the intake tube may be provided for this purpose. In the construction shown, the inner end of the intake tube 10 is flared, and the inlet end of the outlet tube is correspondingly tapered to permit the two tube ends to telescope together in a fluid-tight manner. To promote a fluid-tight fit, one of the two tube ends may be made of relatively soft rubber-like material and may be formed with thin circumferential ribs for sealing contact with the other tube end.

Any suitable means may be provided to close the outlet end of the outlet tube 14 when the outlet tube is not connected to a vacuum source. For example, a suitable plug 18 for closing the outlet port of the outlet tube 14 may be connected to the outlet tube by an elongated flexible strip 20 that is integral with the outer wall of said outlet tube.

When the device is employed for suction drainage from the patient's stomach, the inner end of the outlet tube 14 is telescoped into the inner end of the intake tube 10, as shown in FIG. 1, and the suction tube 15 is employed as shown in FIG. 1 to connect the outlet port of the outlet tube 14 to the wall fitting of a conventional vacuum system. Thus, the outlet tube 14 cooperates with the intake tube 10 to form a continuous channel to the vacuum source.

When it is desired to terminate suction drainage to permit continued spontaneous drainage from the patient's stomach, the inner end of the outlet tube 14 is withdrawn from the inner end of the intake tube 10, as shown in FIG. 2, to permit spontaneous flow from the stomach to empty into the reservoir 16. At this time the plug 18 closes the outlet port of the outlet tube 14. It is obvious, of course, that the outlet tube 14 may be closed by means other than a plug 18. For example, the outer end of the outlet tube may be closed by a clamp, or the outer end of the outlet tube may be lengthened somewhat to permit the outer end to be bent back on itself and releasably secured in bent state.

This first embodiment of the invention affords numerous advantages over prior practices. When suction drainage is stopped to prevent undue irritation of the stomach lining, the closure of the outlet port of the outlet tube 14 by the plug 18, as shown in FIG. 2, prevents release of the drained fluid to the environment, but nevertheless spontaneous drainage from the stomach continues into the reservoir 16. In contrast, if a conventional naso-gastric tube is employed, plugging the outlet port of the device to prevent escape of the drainage to the environment also prohibits spontaneous drainage from the stomach. Thus, the present device makes it possible to continue drainage from the stomach for an indefinite period of time without serious damage to the stomach by prolonged use of a vacuum to maintain drainage.

If the flexible reservoir 16 tends to be filled by the spontaneous flow from the stomach, it is a simple matter to remove the plug 18 from the outlet port of the outlet tube temporarily and to substitute the suction tube 15 briefly to empty the reservoir. With the flexible reservoir made of transparent or nearly transparent material, the interior of the reservoir may be kept under observation, and the transparency makes it a simple matter to maneuver the inner end of the outlet tube 14 into engagement with the inner end of the intake tube 10.

If the intake tube 10 is a well-known type of catheter for draining the bladder into a receptacle or gravity drainage system and is equipped with the usual inflatable cuff for sealing contact with the surrounding wall of the urethra, the drainage device has special utility when it is disconnected from the receptacle or gravity drainage system for the purpose of giving the patient freedom to move away from his hospital bed. At such a time, it is a simple matter to plug the outlet port of the outlet tube 14, as shown in FIG. 2, to prevent any leakage of the drainage to the environment. With the inner end of the outlet tube 14 withdrawn from the inner end of the intake tube 10, spontaneous drainage from the bladder is caught by the reservoir 16.

Figure 3:
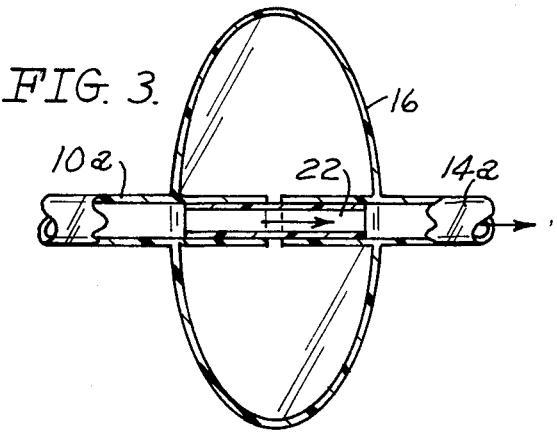
FIGS. 3 and 4 are fragmentary sectional views illustrating another arrangement that permits the confronting ends of the two tubes to be releasably telescoped together.
Figure 4:
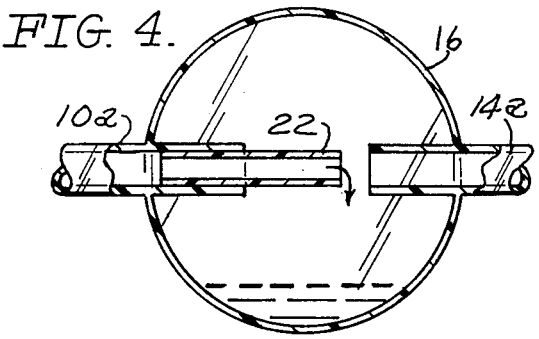

FIGS. 3 and 4 illustrate a simple construction that provides for releasably interconnecting the confronting ends of the intake tube and the outlet tube, respectively. In the construction shown, a short nipple 22 is permanently mounted in the inner end of the intake tube 10a in the manner shown in FIG. 4. For drainage from the intake tube into the reservoir 16, the confronting ends of the intake tube 10a and the outlet tube 14a are separated as shown in FIG. 4. For normal drainage from the body cavity, however, the protruding end of the nipple 22 is telescoped into the outlet tube 14a, as shown in FIG. 3.

Figure 5:
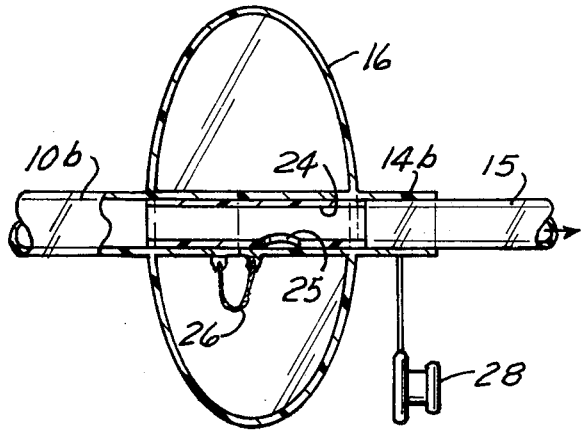
FIG. 5 is a fragmentary sectional view showing a three-way valve interposed between the confronting ends of the intake tube and the outlet tube, the valve being adjusted for suction drainage of a body cavity by a vacuum source.
Figure 6:
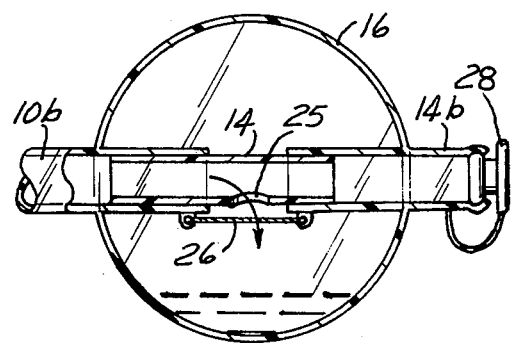
FIG. 6 is a view similar to FIG. 5 showing the three-way valve adjusted to divert the flow from the intake tube into the flexible reservoir.

FIGS. 5 and 6 illustrate how a three-way valve may be incorporated in the structure of FIG. 1, which valve is operable in one respect for suction drainage of the body cavity and is operable in the opposite respect to divert the fluid from the body cavity into the reservoir 16. Fixedly mounted in the end of the intake tube 10b is a nipple 24 that slidingly extends into the end of the outlet tube 14b and is provided with a radial port 25. A filament 26, which may be a piece of string, is anchored at its opposite ends to the intake tube 10b and the outlet tube 14b, respectively, which string is pulled taut, as shown in FIG. 6, to limit the extent to which the nipple 24 may be retracted from the outlet tube 14b. Thus, the string 26 prevents complete disengagement of the nipple 24 from the outlet tube 14b and at the same time determines one of the two limit positions of the nipple relative to the outlet tube, as may be seen in FIG. 6. At the other limit position of the nipple 24, shown in FIG. 5, the end of the intake tube 10b abuts against the end of the outlet tube 14b, the outlet tube serving as a stop.

During normal drainage of the body cavity either by gravity or by means of a vacuum, the valve structure is in the normal position shown in FIG. 5, where the radial port 15 of the nipple 24 is closed by the surrounding wall of the outlet tube 14b. At this adjustment of the valve structure, the intake tube is in direct communication with the outlet tube to bypass the reservoir 16. At the other limit position of the valve structure shown in FIG. 6, the radial port 15 of the nipple 24 is open to the reservoir 16 to divert the drainage flow into the reservoir, and at this time the outlet port of the outlet tube is suitably closed, for example, by means of a plug 28, to prevent any leakage of the drainage fluid to environment. Since the intake tube and the outlet tube cannot be pulled apart, the wall of the reservoir 16 need not be transparent.

FIGS. 7–9 illustrate another embodiment of the invention that is largely identical with the embodiment shown in FIGS. 1 and 2, as indicated by the use of corresponding reference numerals to designate corresponding parts. The intake tube 10c is divided into two sections 30 and 31 that are interconnected by a quick disconnect joint 32. As shown in FIG. 7, the quick-disconnect joint 32 is provided by a short nipple 34, which is permanently mounted in the end of one of the two sections 30 and 31 and retractably telescopes into the other section.

This embodiment of the invention also includes a tubular needle 35, which is open at both ends and is formed with an inclined cutting edge 36 at its leading end. The tubular needle 35 is slightly curved near its trailing end, as shown, and is provided with a handle at its trailing end which may be in the form of a ring 38. The tubular needle 35 may be aptly termed a pilot needle since it serves as means to guide the leading end of the tube section 30 into the region of the body cavity.

FIG. 8, for example, shows how the tubular needle may be inserted into the flesh of a patient to reach an abscess 40. With the tubular needle 35 in the position shown in FIG. 8, it is a simple matter to insert the section 30 of the intake tube 10c through the needle into the abscess. Once the section 30 of the intake tube 10c is in communication with the abscess, as shown in FIG. 9, the tubular pilot needle 35 may be retracted along the section 30; and with the two sections 30 and 31 separated, it is a simple matter to retract the hollow needle until it is completely free both from the tube section 30 and the tube section 31. Thereafter, the quick-disconnect joint may be closed for normal drainage operation of the device in the manner heretofore described.

FIG. 10 illustrates an embodiment of the invention in which the usual intake tube is replaced by a special tube 42, which serves both as means for draining a body cavity and irrigating the body cavity. An intermediate portion of the length of the tube 42 is provided with perforations or radial ports 44, and the far end of the tube is somewhat enlarged and is provided with a removable plug 45 of the character heretofore described. The tube 42 is made in two separate sections which are normally interconnected by a quick-disconnect joint 32.

When a wound in the flesh of a patient is closed in the usual manner by sutures 46 and covered by a bandage 47, the perforated intermediate portion of the tube 42 is laid in the wound before the wound is closed with both ends of the tube extending to the exterior as shown. With the far end of the tube 42 closed by the plug 45, the tube 42 may be used for vacuum drainage of the healing zone below the sutures 46 in the manner heretofore described. Whenever it is desired to irrigate the wound, the plug 45 is removed and irrigation fluid is introduced into the far end of the tube for removal by suction drainage. When the wound has healed to a satisfactory extent, the quick-disconnect joint 32 may be pulled apart to permit the two sections of the tube 42 to be withdrawn from opposite ends of the wound.

An important advantage of the arrangement shown in FIG. 10 is that the bandage is kept dry. A bandage that is wet with drainage is unsatisfactory and has an offensive odor.

In the embodiment of the invention shown in FIG. 11, the intake tube 48 of the device and the outlet tube 50 are permanently united to form a constantly open passage to the outlet port 52 of the outlet tube. A suitable plug 54 on a flexible strip 55 is provided to close the outlet port 52 whenever desired.

The outlet tube 50 is formed with a downwardly directed nipple or neck 56. The flexible reservoir in this embodiment is in the form of a flexible bag 58, which is releasably mounted on the neck 56 of the tube 50, for example, by means of a conventional resilient ring-shaped clamp 60.

It is apparent that the reservoir 58 is never isolated from the intake tube 48 so that drainage from the intake tube into the reservoir is possible at all times. Thus, there is no need to manipulate a valve or to break a tube connection to permit flow from the intake tube 48 into the reservoir.

During normal suction operation of the device, the flexible reservoir 58 is collapsed by the suction and the drainage fluid is drawn directly from the intake tube 48 to whatever suction tube is connected to the outlet port 52 of the outlet tube 50. Whenever it is desirable to interrupt the vacuum drainage of the body cavity, the outlet port is simply closed by the plug 54 to permit drainage from the intake tube 48 to gravitate into the reservoir bladder 58. When vacuum operation is subsequently resumed, the suction initially collapses and evacuates the reservoir bladder 58, and thereafter the vacuum draws drainage fluid directly from the intake tube 48.

FIG. 12 illustrates an embodiment of the invention that provides for both drainage and irrigation of a body cavity. The device is illustrated as similar in construction to the embodiment shown in FIG. 11, but it is to be understood that the construction may be similar to that of the embodiment shown in FIGS. 1 and 2.

The construction shown in FIG. 12 differs from the construction shown in FIG. 11 in that a double tube or dual passage tube, generally designated 62, is substituted for the usual single intake tube. One tube or passage 64 is provided with the usual intake apertures 65 and is directly and permanently connected to the outlet tube 50. The other tube or passage 67 has discharge apertures 66 at its far end and at its near end is normally closed by a plug 68. Thus the second tube or passage 67 is available whenever it is desirable to inject irrigation fluid into the body cavity.

FIGS. 13–15 illustrate a valve structure that is of the general character of the valve structure shown in FIGS. 5 and 6, but which provides for automatically cutting off the outlet port of the device whenever the valve is adjusted to divert drainage flow into the flexible reservoir 16.

The inner end of the intake tube 10c in FIGS. 13 and 14 has a nipple extension 70 that is closed at its outer end by an end wall 72 and is formed with both a lower radial aperture 74 and an upper radial aperture 75 spaced forwardly from the lower aperture. As in the previously described embodiment shown in FIGS. 5 and 6, a filament or string 26 pulls taut, as shown in FIG. 14, to limit the retraction of the nipple extension 70 from the structure of the outlet tube 14c.

The outlet tube 14c has a blind tubular portion 76, in which the nipple extension 70 is slidingly mounted, and has an adjacent tubular outlet portion 78 that is formed with an outlet port 80 for connection to a vacuum source by the usual vacuum tube 15. The wall 82 that separates the two tubular portions 76 and 78 of the outlet tube 14c is provided with an aperture 84 for cooperation with the aperture 75 of the nipple extension 70. The nipple extension 70 is formed with a longitudinal rib 85 that slides in a corresponding groove in the tubular portion 76 of the outlet tube to prevent rotation of the nipple extension. The end of the blind tubular portion 76 is provided with a small vent bore 77 to prevent the formation of a vacuum therein when the nipple extension 70 is retracted.

When the device is used for suction drainage, the valve structure is adjusted at the limit position shown in FIG. 13 with the end of the intake tube 10c in abutment with the end of the tubular portion 76 of the outlet tube 14c and the radial aperture 75 of the nipple extension 70 in registration with the aperture 84 of the outlet tube, as shown in FIGS. 13 and 15, to place the intake tube 10c in direct communication with the vacuum source through the vacuum tube 15. At this time the lower radial aperture 74 of the nipple extension 70 is closed by the surrounding wall of the tubular portion 76 of the outlet tube, as shown in FIG. 13. Thus, at the advanced adjustment of the valve structure shown in FIG. 13, drainage flow from the intake tube 10c is directed to the outlet tube 14c. At the alternate retracted position of the valve structure shown in FIG. 14, the aperture 84 of the outlet tube is closed to cut off the outlet port 80 and at the same time the lower radial port 74 of the nipple extension is unmasked to divert drainage flow from the intake tube 10c into the flexible reservoir 16.

One advantage of the modification shown in FIGS. 13 and 14 is that it eliminates the need for a plug to close the outlet port 80, as well as the need for manipulating such a plug. When the valve structure is adjusted as shown in FIG. 14 to cut off the outlet port 80 and simultaneously to divert the drainage flow into the reservoir 16, the suction tube 15 may be withdrawn from the outlet port 80 to make the patient independent of the vacuum source, and as the vacuum tube 15 is withdrawn, it tends to suck up any residual liquid that may be present in the now blind tubular portion 78 of the outlet tube. Ordinarily, no significant amount of residual fluid remains at the outlet port 80, but if desired a piece of cotton or cleansing tissue may be inserted to dry the outlet port. Here again, as in the valve structure shown in FIGS. 5 and 6, the string 26 prevents complete disconnection of the intake tube 10c from the outlet tube 14c, and, therefore, it is not necessary that the reservoir 16 be made of transparent material.

My description in specific detail of the selected embodiments of the invention will suggest various changes, substitutions, and other departures from my disclosure within the spirit and scope of the appended claims.

I claim:

1. In a device for use with drainage means to carry out a procedure that includes withdrawing fluid from a cavity in the body of a patient, the combination of:
   an intake tube for insertion into the cavity having coupling means at its outer end;
   means including an outlet tube for cooperation with the intake tube to form a passage means from the intake tube for the drainage fluid,
   said outlet tube having an outlet port at the outer end thereof for release of the drainage fluid and coupling means at its other end for cooperating with said intake tube coupling means;
   means for opening and closing said outlet port; and
   a reservoir means encompassing said coupling means, said passage means being designed so that it can be opened by actuation of said coupling means, and said reservoir means being in communication with said passage means to receive fluid from the intake tube when the outlet port is closed and said coupling means are actuated to open said passage means.

2. A combination as set forth in claim 1 in which the means for opening and closing the outlet port is a plug to retractably fit into the outlet port.

3. A combination as set forth in claim 1 in which said reservoir encloses both the outer end of the intake tube and the outer end of the outlet tube.

4. A combination as set forth in claim 3 in which said reservoir is flexible to permit the outlet tube to be connected directly to the intake tube via said coupling means to place the intake tube in direct communication with said outlet port when the outlet port is open and to permit the outlet tube to be spaced away from the intake tube to permit fluid from the intake tube to flow into the reservoir when the outlet port is closed.

5. A combination as set forth in claim 4 in which the outer end of the intake tube and the inner end of the outlet tube, respectively, are shaped and dimensioned to releasably telescope together.

6. A combination as set forth in claim 3 in which said coupling means includes valve means inside the reservoir to place the intake tube in communication with the outlet tube and the reservoir selectively.

7. A combination as set forth in claim 6 in which said valve means includes a hollow member united with one of the two tubes and slidable in the end of the other of the two tubes between an advanced position and a retracted position,
   said hollow member having a radial port for communication with the reservoir,
   said radial port being open at the retracted position of the hollow member and being closed by said other of the two tubes at the advanced position of the hollow member.

8. A combination as set forth in claim 7 which includes means to limit the retraction of the hollow member to prevent withdrawal of the hollow member from said other of the two tubes.

9. A combination as set forth in claim 8 in which said means to limit the retraction of the hollow member is a flexible filament connected to both of the two tubes.

10. A combination as set forth in claim 8 in which said hollow member has a second radial port that is closed by said other of the two tubes at the retracted position of the hollow member to cut off said outlet port of the outlet tube, said second radial port being in communication with the outlet port of the outlet tube at the advanced position of the hollow member.

11. A combination as set forth in claim 3,
    which includes valve means in the reservoir adjustable in one respect to place the intake tube in communication with the reservoir and simultaneously cut off the outlet port from the reservoir,
    said valve means being adjustable in the opposite respect to open the outlet port and to place the intake tube in communication with the outlet port and simultaneously cut off the intake tube from the reservoir.

12. A combination as set forth in claim 1 which includes a tubular needle telescopically received over the far end of the intake tube to facilitate insertion of said far end into the body of the patient.

13. A combination as set forth in claim 12 in which the intake tube is made in two sections normally interconnected by a releasable joint so that after the tubular needle facilitates insertion of the far end of the intake tube, and said joint is opened, the tubular needle may be withdrawn and freed from the intake tube at the open joint, and then the joint may be closed for a drainage operation.

14. A combination as set forth in claim 1 in which an intermediate portion of the intake tube is apertured for fluid intake and the far end of the intake tube is open, so that with the intermediate portion of the intake tube inside a cavity of the body of a patient and the far end of the intake tube outside the body of the patient, the far end of the intake tube may be closed during suction drainage of the body cavity or fluid may be introduced into the outer end of the intake tube to irrigate the body cavity.

15. A combination as set forth in claim 14 which includes means to releasably close the far end of the intake tube.

16. A combination as set forth in claim 1 which includes an irrigation tube united with the intake tube in side-by-side relationship for insertion into the body cavity along with the intake tube,
    said irrigation tube being apertured to introduce irrigation fluid into the body cavity,
    the near end of the irrigation tube being normally closed to permit drainage of the body cavity by the intake tube but available, as desired, to receive irrigation fluid.

* * * * *